US009579165B2

(12) United States Patent
Lavelle

(10) Patent No.: US 9,579,165 B2
(45) Date of Patent: Feb. 28, 2017

(54) SURGICAL TRAY CORNER PROTECTOR

(76) Inventor: Richard M. Lavelle, Pittsburgh, PA (US)

( * ) Notice: Subject to any disclaimer, the term of this patent is extended or adjusted under 35 U.S.C. 154(b) by 1260 days.

(21) Appl. No.: 11/846,132

(22) Filed: Aug. 28, 2007

(65) Prior Publication Data

US 2008/0179209 A1 Jul. 31, 2008

Related U.S. Application Data

(60) Provisional application No. 60/898,046, filed on Jan. 29, 2007.

(51) Int. Cl.
*B65D 1/34* (2006.01)
*B65D 81/05* (2006.01)

(52) U.S. Cl.
CPC .............. *A61B 50/33* (2016.02); *A61B 50/30* (2016.02); *B65D 81/053* (2013.01)

(58) Field of Classification Search
CPC .. B65D 81/053; B65D 81/054; B65D 81/055; B65D 81/056; A61B 50/33
USPC ..... 206/586, 77.1, 587, 588; 248/345.1, 453
See application file for complete search history.

(56) References Cited

U.S. PATENT DOCUMENTS

| 1,320,205 A | 10/1919 | Cochrane |
|---|---|---|
| 1,546,680 A | 7/1925 | Sessions |
| 2,080,630 A | 5/1937 | Nathanson |
| 3,030,728 A | 4/1961 | Wesman |
| 2,995,863 A | 8/1961 | Bright |
| 3,137,087 A | 6/1964 | Shroyer |
| 3,655,113 A | 4/1972 | Carroll |
| 3,725,188 A | 4/1973 | Kalt |
| 3,762,626 A | 10/1973 | Dorsey |
| 3,822,036 A | 7/1974 | Goodsite |
| 3,843,038 A | 10/1974 | Sax |
| 3,870,152 A | 3/1975 | Kaplan |
| 3,955,677 A | 5/1976 | Collingwood |
| 3,960,354 A | 6/1976 | Simikoski |
| 3,975,564 A | 8/1976 | Jones |
| 3,994,433 A | 11/1976 | Jenkins et al. |
| 4,072,231 A | 2/1978 | Helms |
| D249,314 S | 9/1978 | Wilde et al. |
| D253,506 S | 11/1979 | Vigue |
| D260,590 S | 9/1981 | Hobson |

(Continued)

FOREIGN PATENT DOCUMENTS

| EP | 0143299 | 6/1985 |
|---|---|---|
| EP | 1357056 | 10/2003 |

(Continued)

OTHER PUBLICATIONS

HMARK, UnderGuard Tray Corners, 2006, p. 19, US.

*Primary Examiner* — Anthony Stashick
*Assistant Examiner* — Robert Poon
(74) *Attorney, Agent, or Firm* — Trego, Hines & Ladenheim, PLLC; Brandon Trego; Jonathan Hines

(57) ABSTRACT

A corner protector for use with a surgical tray includes a base, at least one side extending from the base, and at least one aperture extending through the base. The at least one aperture allows a medium to pass therethrough. The corner protector further includes at least one stud extending from a major surface of the corner protector such that when the corner protector is positioned against a surgical tray, a channel is created between the corner protector and the surgical tray.

11 Claims, 16 Drawing Sheets

(56) References Cited

U.S. PATENT DOCUMENTS

| | | | |
|---|---|---|---|
| 4,287,265 A | 9/1981 | McKnight | |
| 4,496,054 A | 1/1985 | Koltun | |
| 4,529,091 A | 7/1985 | Martin | |
| D287,446 S | 12/1986 | Cowle | |
| 4,742,916 A | 5/1988 | Galea | |
| 4,838,427 A | 6/1989 | Hurley | |
| 4,851,286 A | 7/1989 | Maurice | |
| 4,852,744 A | 8/1989 | Van Breemen | |
| 5,175,041 A | 12/1992 | Webb et al. | |
| 5,226,626 A * | 7/1993 | Driscoll | 248/343 |
| 5,297,682 A | 3/1994 | Miltenberger | |
| 5,311,825 A | 5/1994 | Bonham | |
| 5,370,229 A | 12/1994 | Kroeckel et al. | |
| D356,946 S | 4/1995 | Rekuc | |
| 5,549,868 A | 8/1996 | Carlson, II | |
| D384,585 S | 10/1997 | Swarr | |
| 5,749,512 A | 5/1998 | Gingras-Taylor | |
| 5,772,037 A | 6/1998 | Hurley | |
| D416,476 S | 11/1999 | Engberg | |
| 6,007,469 A | 12/1999 | Jaegers et al. | |
| 6,039,184 A | 3/2000 | Gale | |
| 6,103,335 A * | 8/2000 | Zoller et al. | 428/116 |
| 6,368,694 B1 | 4/2002 | Marsh et al. | |
| 6,440,375 B1 | 8/2002 | Davis et al. | |
| 6,470,637 B2 | 10/2002 | Gratz | |
| 6,478,354 B1 | 11/2002 | Eyal | |
| 6,629,608 B2 | 10/2003 | Hurley et al. | |
| 6,776,380 B1 | 8/2004 | Kirk, Jr. et al. | |
| 6,840,372 B2 | 1/2005 | Giles et al. | |
| 6,902,712 B2 | 6/2005 | Davis | |
| D537,337 S | 2/2007 | Brockington et al. | |
| 7,413,157 B2 | 8/2008 | Curnow et al. | |
| 7,422,185 B2 | 9/2008 | Curnow et al. | |
| 2005/0244316 A1 | 11/2005 | Davis | |
| 2006/0243636 A1 | 11/2006 | Robichaud et al. | |
| 2007/0039848 A1* | 2/2007 | Burchell | 206/453 |

FOREIGN PATENT DOCUMENTS

| | | |
|---|---|---|
| WO | WO94/10058 | 5/1994 |
| WO | WO 2007/019233 | 2/2007 |

* cited by examiner

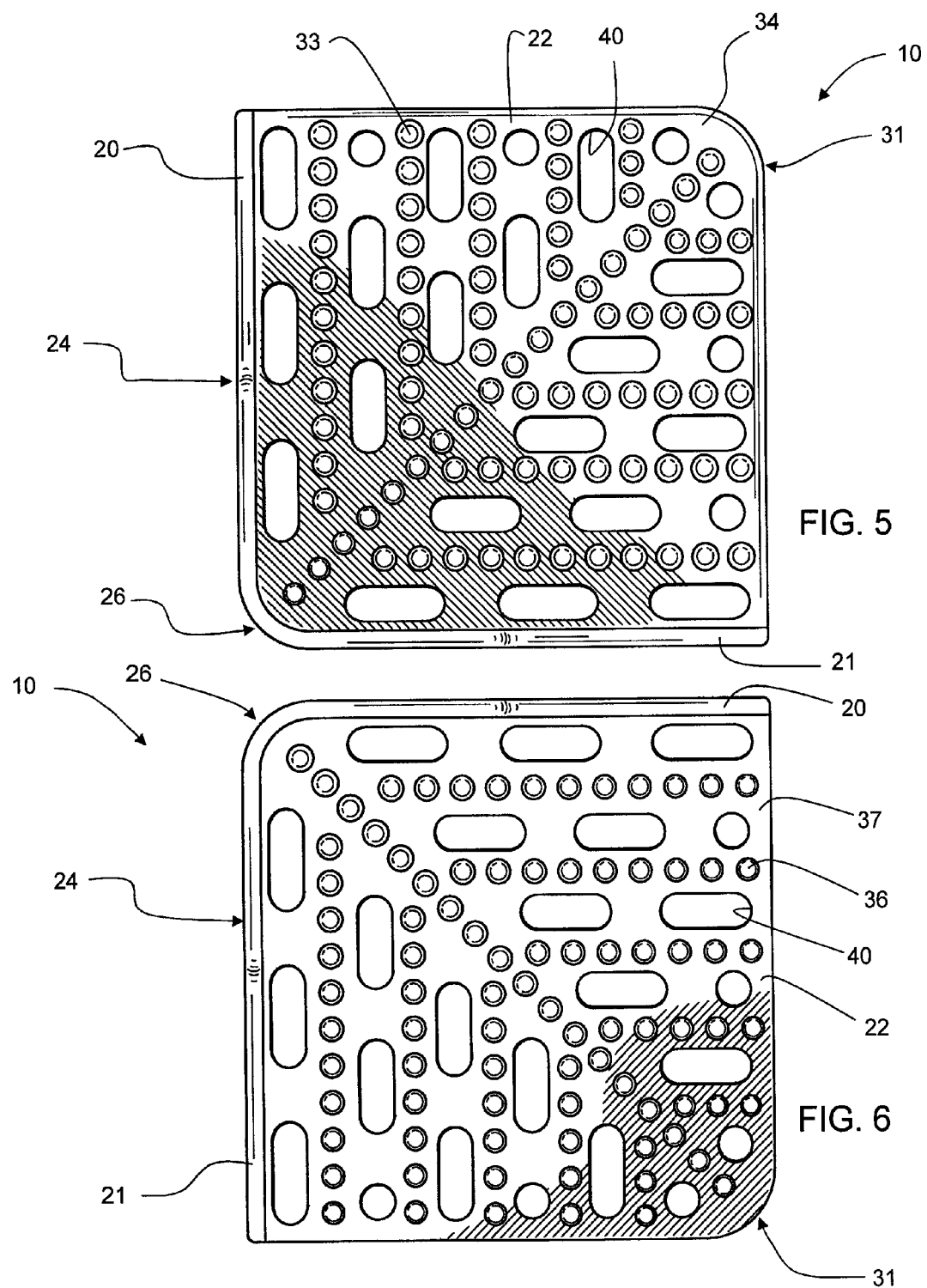

SURGICAL TRAY CORNER PROTECTOR

This application claims the benefit of Provisional Application No. 60/898,046 filed on Jan. 29, 2007.

TECHNICAL FIELD AND BACKGROUND OF THE INVENTION

The present invention relates to the field of corner protectors. In particular, the invention relates to corner protectors for use with surgical trays.

Surgical trays are used to organize, sterilize, and carry surgical instruments into an operating room for use by a surgeon. Because the surgical trays and instruments carry pathogens, the trays and instruments must be sterilized prior to being placed in the operating room. This is done by placing the instruments in the trays, wrapping the trays in sterile wraps, as shown in FIG. 1, and placing the wrapped trays in a sterilization chamber where a sterilization agent such as steam, gas, or plasma is used to sterilize the trays and instruments. The wrapped trays are then carried to the operating room for use.

Unfortunately, after the sterilization process has taken place, it is often discovered that the feet of the trays have punctured through the sterile wrap, as shown in FIG. 2, causing the trays and instruments contained therein to be contaminated. If a surgical instrument tray and the instruments therein cannot be used because the foot of the tray or corner punctured the sterilization wrap, the surgery might have to be delayed or possibly canceled, costing the hospital or surgery center time, money and frustration for both the staff and physicians.

SUMMARY OF THE INVENTION

Accordingly, the above-noted shortcomings of the prior art are addressed by the present invention, which provides a surgical tray corner protector that can prevent the feet of a surgical tray from puncturing the wrap, while allowing circulation of the sterilization agent between the tray and the wrap.

According to one aspect of the invention, a corner protector includes a base, at least one side extending from the base, at least one aperture extending through the base for allowing a medium to pass therethrough, and at least one stud extending from a major surface of the corner protector. The stud is positioned on the major surface such that when the corner protector is positioned against an object, a channel is created between the corner protector and the object.

According to one aspect of the invention, a surgical tray corner protector includes a base, a pair of sides extending from the base, and a plurality of apertures extending through the base for allowing a medium to pass therethrough. The corner protector further includes a plurality of studs disposed on a bottom of the base to provide support to the base and prevent the base from bottoming out when a surgical tray is placed on the base and maintain a channel for the medium to pass through.

According to another aspect of the invention, a surgical tray corner protector includes a base having a plurality of apertures extending through the base for allowing a medium to pass therethrough, a side extending from the base having a first side portion and a second side portion, and at least one stud extending from the side. When the corner protector is in an installed position, the at least one stud rests against the tray, thereby creating a channel between the side and the tray to allow the medium to pass therebetween.

BRIEF DESCRIPTION OF THE DRAWINGS

The invention may be best understood by reference to the following description in conjunction with the accompanying drawing figures in which:

FIG. 5 is a top view of the corner protector of FIG. 4;
FIG. 6 is a bottom view of the corner protector of FIG. 4.

DESCRIPTION OF THE PREFERRED EMBODIMENT AND BEST MODE

Figure 1:
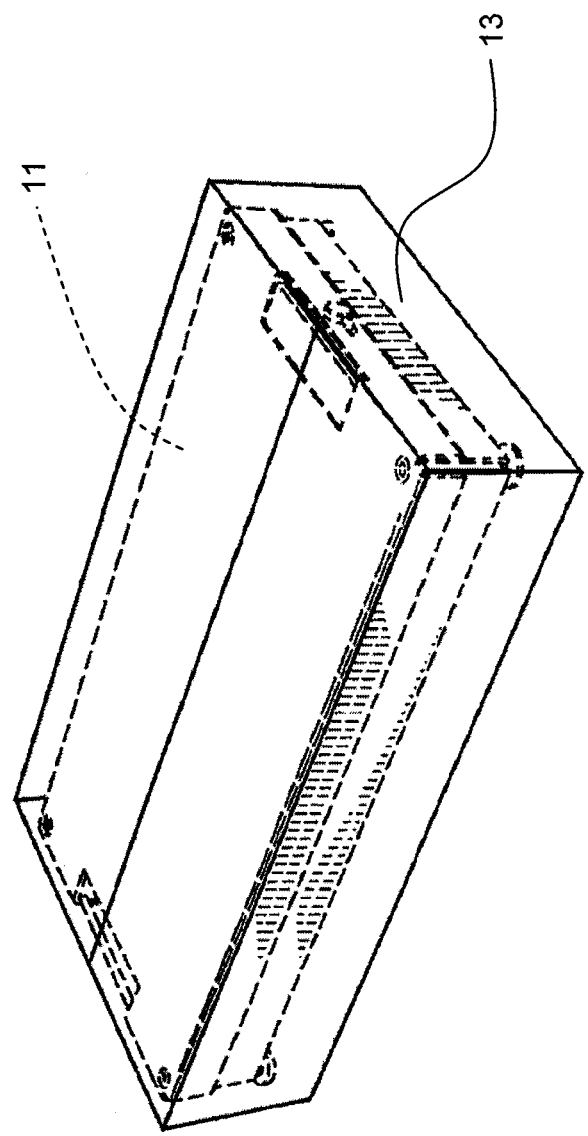
FIG. 1 shows a surgical tray wrapped in a sterile wrap.
Figure 2:
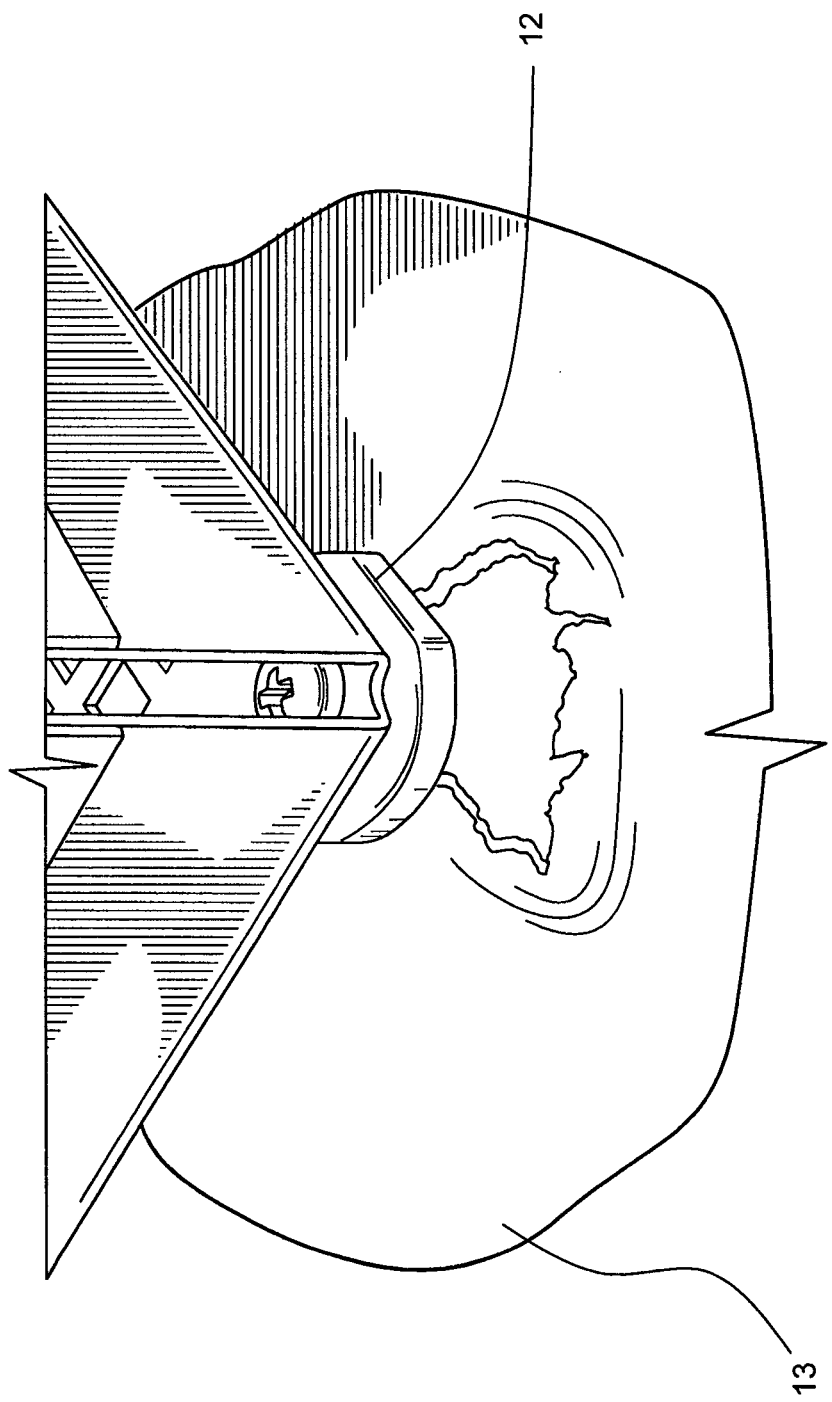
FIG. 2 shows the sterile wrap punctured by a foot of the surgical tray of FIG. 1.
Figure 3:
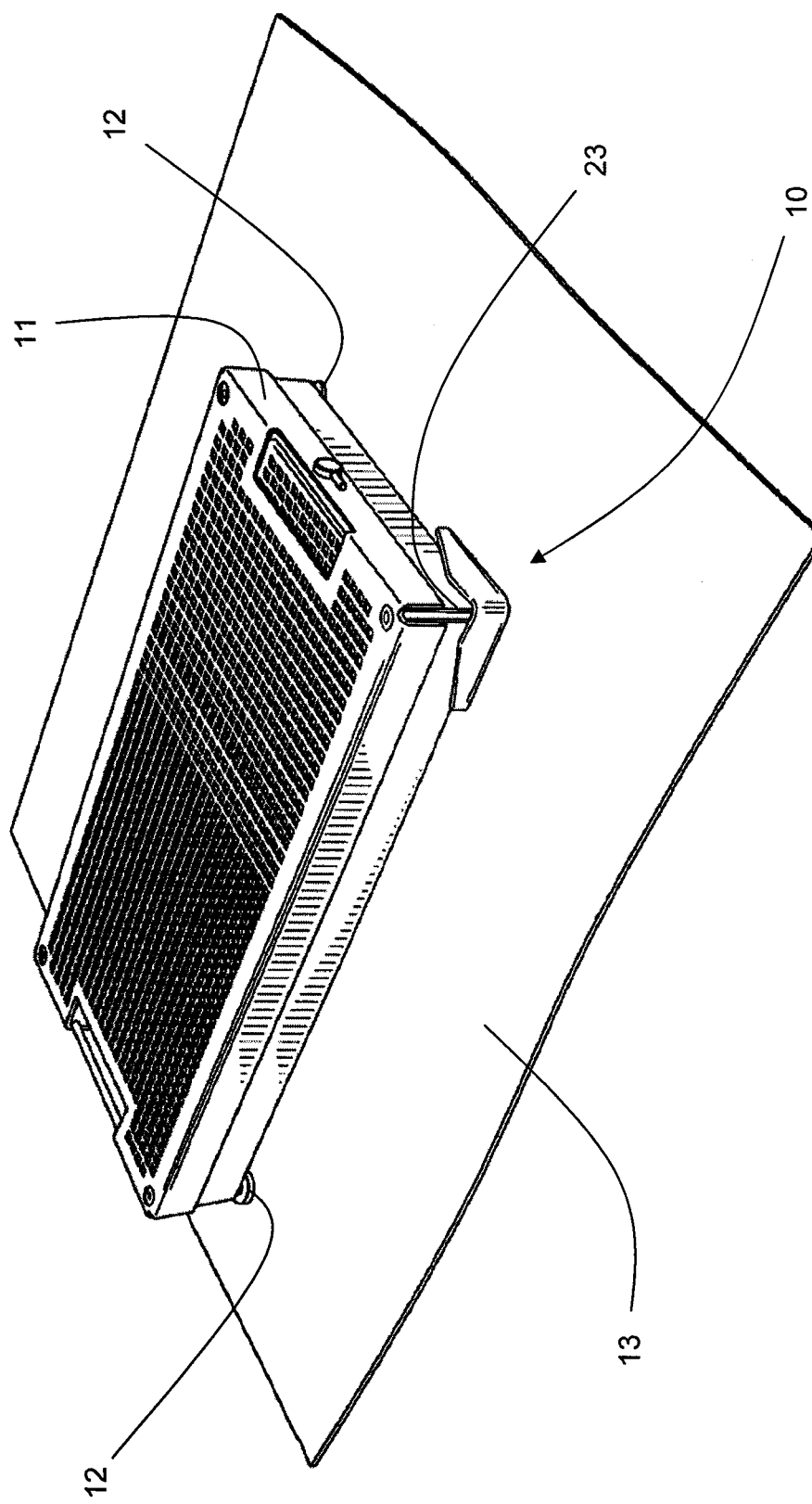
FIG. 3 shows the surgical tray of FIG. 1 placed on a sterile wrap using a corner protector according to an embodiment of the invention.

Referring now specifically to the drawings, a surgical tray corner protector according to an embodiment of the invention is illustrated in FIG. 3 and shown generally at reference numeral 10. The corner protector 10 is designed to be placed on a corner of a surgical tray 11 between a foot 12 of the tray 11 and a sterile wrap 13. The corner protector 10 prevents a foot 12 from puncturing through the sterile wrap 13 as shown in FIG. 2 while allowing a sterilization agent to circulate around the foot 12 and between the sterile wrap 13 and corner protector 10.

Figure 4:
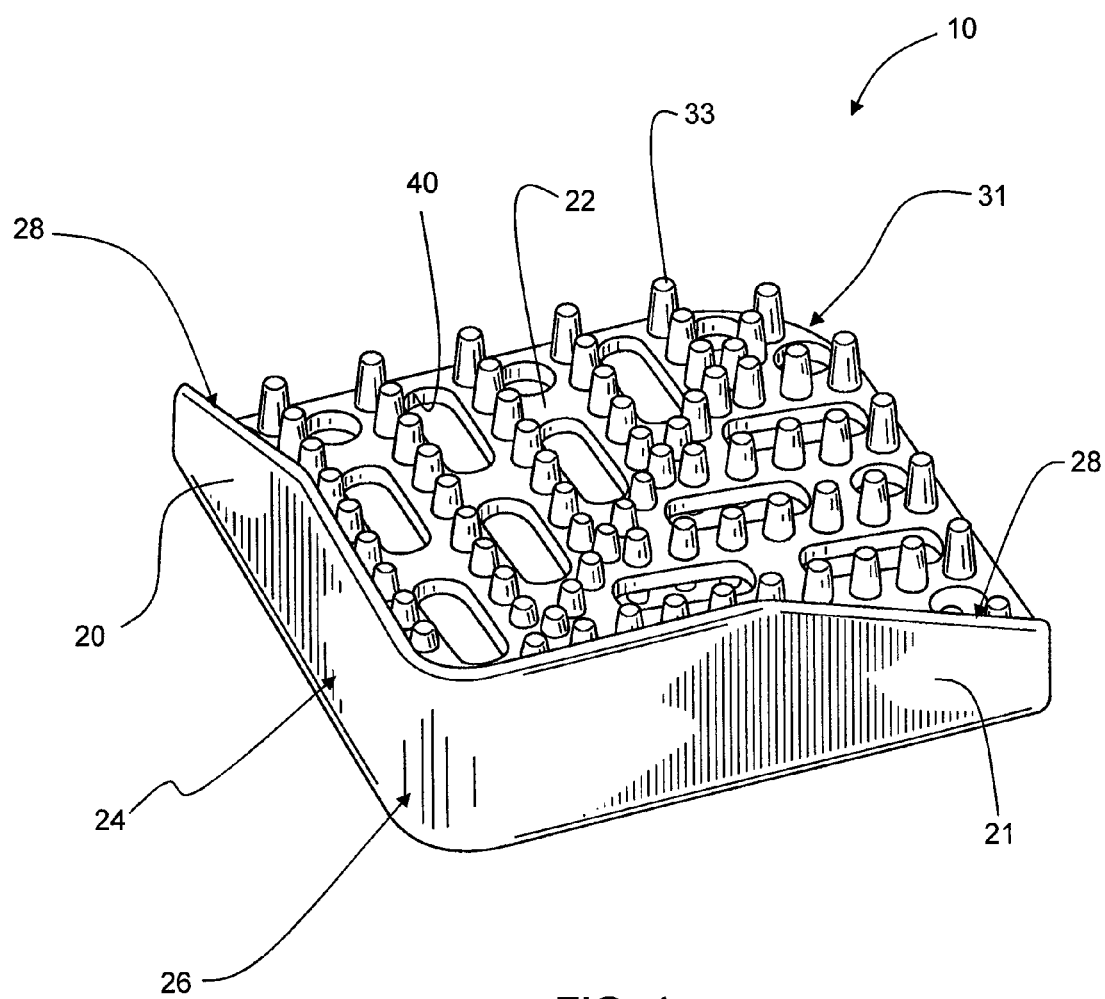
FIG. 4 is a perspective view of the corner protector of FIG. 3.
Figure 7:
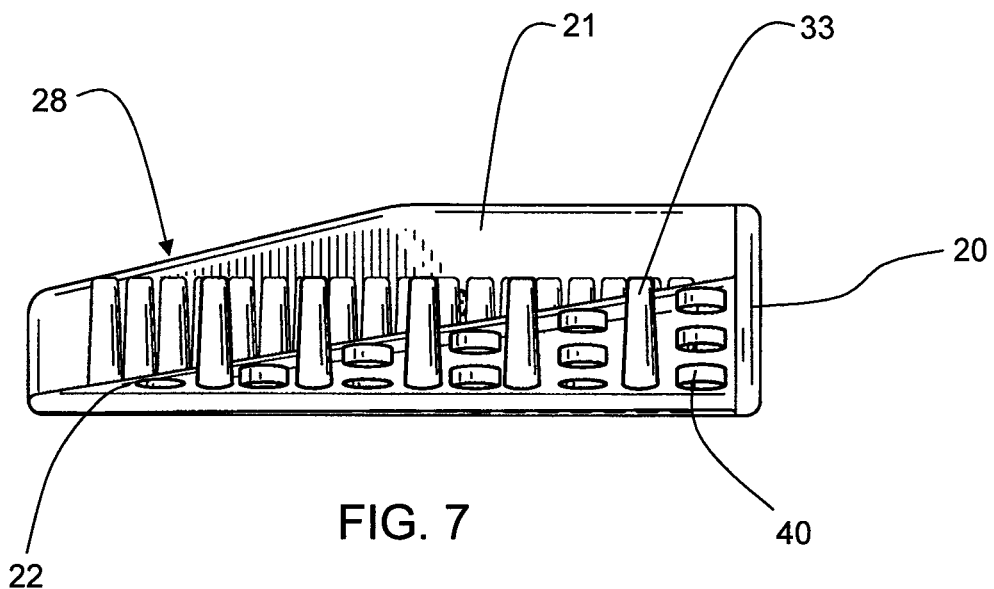
FIG. 7 is a right, front side view of the corner protector of FIG. 4.
Figure 8:
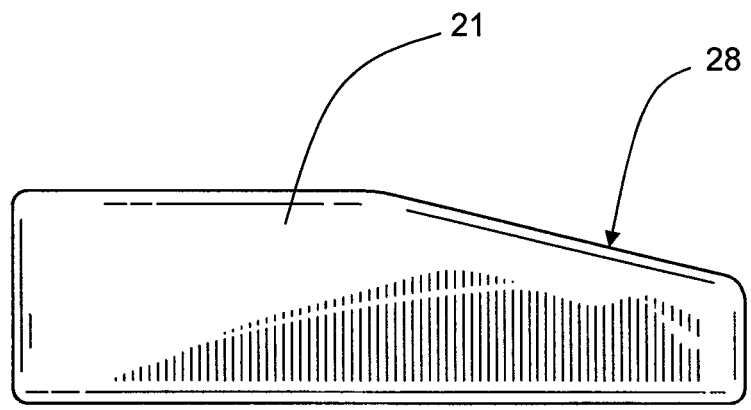
FIG. 8 is a right, rear side view of the corner protector of FIG. 4.
Figure 9:
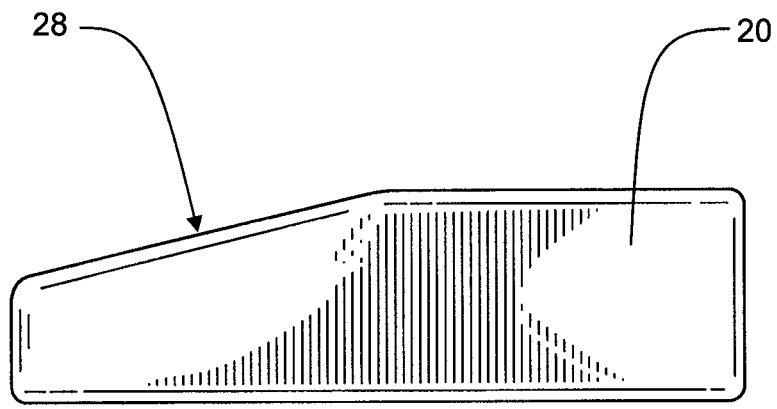
FIG. 9 is a left, rear side view of the corner protector of FIG. 4.

Referring to FIGS. 4-10, the corner protector 10 includes a pair of sides. 20 and 21 extending upwardly from a base 22. The sides 20 and 21 create a soft barrier between sharp corner edges 23 of the tray 11 and the sterile wrap 13 to prevent tearing of the sterile wrap 13. The sides 20 and 21 also allow the corner protector 10 to be used with straight edge or rounded edge surgical trays, enhance stability of the corner protector 10 on the tray 11 prior to wrapping, and keep the corner protector 10 in place while wrapping the surgical tray 11. As shown in FIGS. 4-6, the sides 20 and 21 form a single L-shaped continuous wall 24 with a rounded corner 26. Each of the sides 20 and 21 includes a sloped portion 28, as illustrated in FIGS. 8 and 9, that extends towards an end of each respective side 20 and 21 where protection is less critical to minimize interference of a medium or sterilizing agent with the tray 11 during the sterilization process.

Figure 10:
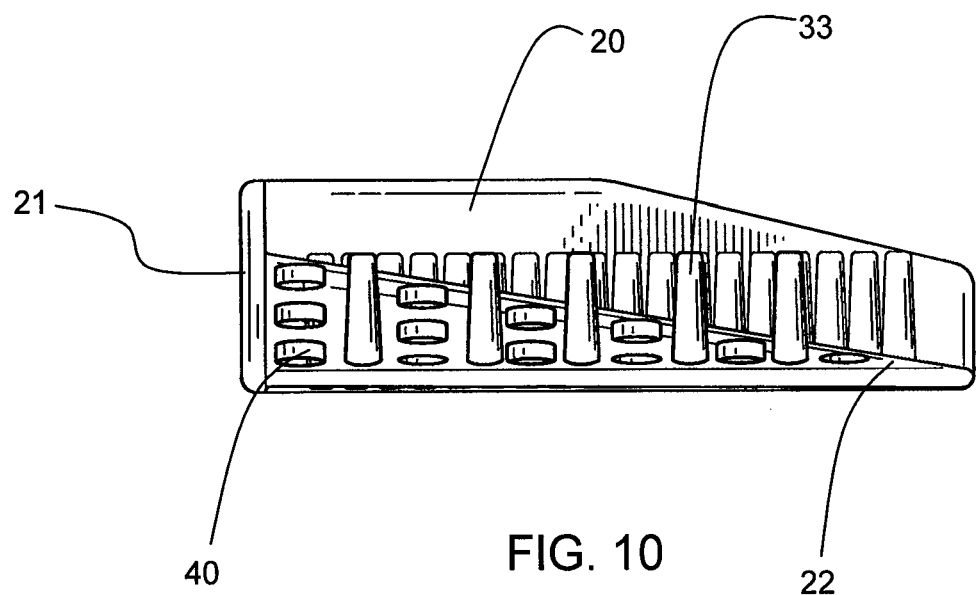
FIG. 10 is a left, front side view of the corner protector of FIG. 4.

The base 22 slopes, as illustrated in FIGS. 7 and 10, downwardly from the corner 26 to a front 31 of the base 22, and includes a plurality of studs 33 that project upwardly from a top 34 of the base 22 and a plurality of studs 36, FIG. 6, that project downwardly from a bottom 37 of the base 22. The length of the studs 33 is longer at the front 31 of the base 22 than at the corner 26. The length of the studs 33 progressively increase in length along the slope (from corner 26 to front 31) of the base 22, such that the studs 33 provide a substantially level plane along a top of the studs 33, as shown in FIG. 7. The length of the studs 36 are in an inverse relationship to that of the studs 33. Thus, the studs 36 are longer at the corner 26 than at the front 31 of the base 22 such that the studs 36 provide a substantially level plane along the ends of the studs 36 for placement on a surface, such as a table.

The studs 33 allow a foot of the surgical tray 11 to sit on top of the base 22 in an elevated posture to enhance circulation of the sterilizing agent between the tray 11 and the base 22 and wrap 13. The studs 33 also allow the sterilization agent to get into the corners of the trays 11, and help ensure better drying time in steam, gas, and plasma sterilization cycles. The studs 36 keep the base 22 of the corner protector 10 elevated off of the sterile wrap 13 to allow circulation of the sterilizing agent between the base 22 and the wrap 13.

The studs 33 and 36 compress to absorb the weight of the tray 11 and keep the tray from bottoming out (i.e. flattening). This prevents a foot of the tray 11 from pressing directly against the sterile wrap 13, thereby providing a barrier between the foot and the wrap 13 and preventing the foot from puncturing the wrap 13. Because the studs 33 and 36 compress and distribute the weight of the tray, a channel for the sterilizing agent to circulate through is maintained. Additionally, the studs 33 and 36 do not fold over or collapse to allow a foot of the tray 11 to press the base 22 against the wrap 13.

A plurality of apertures 40, shown in FIGS. 5 and 6, are formed through the base 22 to allow the sterilization agent to circulate easily between the wrap 13 and the corner protector 10, the corner protector 10 and the surgical tray 11, and the wrap 13 and the surgical tray 11. The apertures 40 prevent the base 22 from inhibiting the circulation of the sterilization agent. Additionally, the apertures 40 help enhance drying times.

The corner protector 10 is made of a medical grade material that does not retain moisture, such as silicone rubber. During the sterilization process of moisture absorbing products, moisture can sometimes remain after the drying period, thereby increasing the ability of water borne pathogens to develop and contaminate the contents of the surgical tray 11. By using a non-moisture absorbing material, water borne pathogens can be prevented. The material also provides a "tackiness" to help keep the corner protector 10 in place on the tray 11, and allows the corner protector 10 to be cut to size for a desired application and disposed of after a single use.

Figure 11:
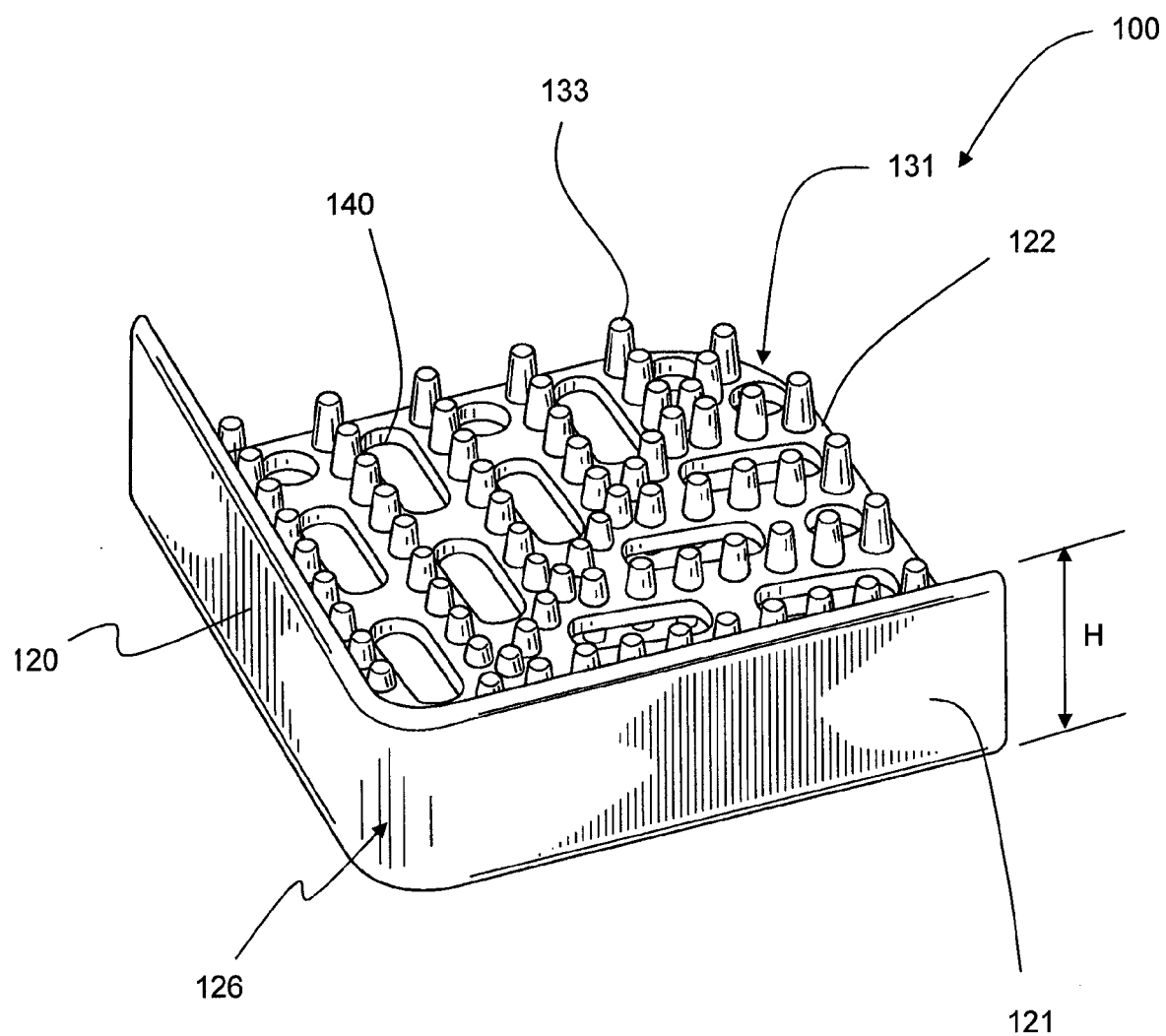
FIG. 11 is a perspective view of a corner protector according to an embodiment of the invention.
Figure 12:
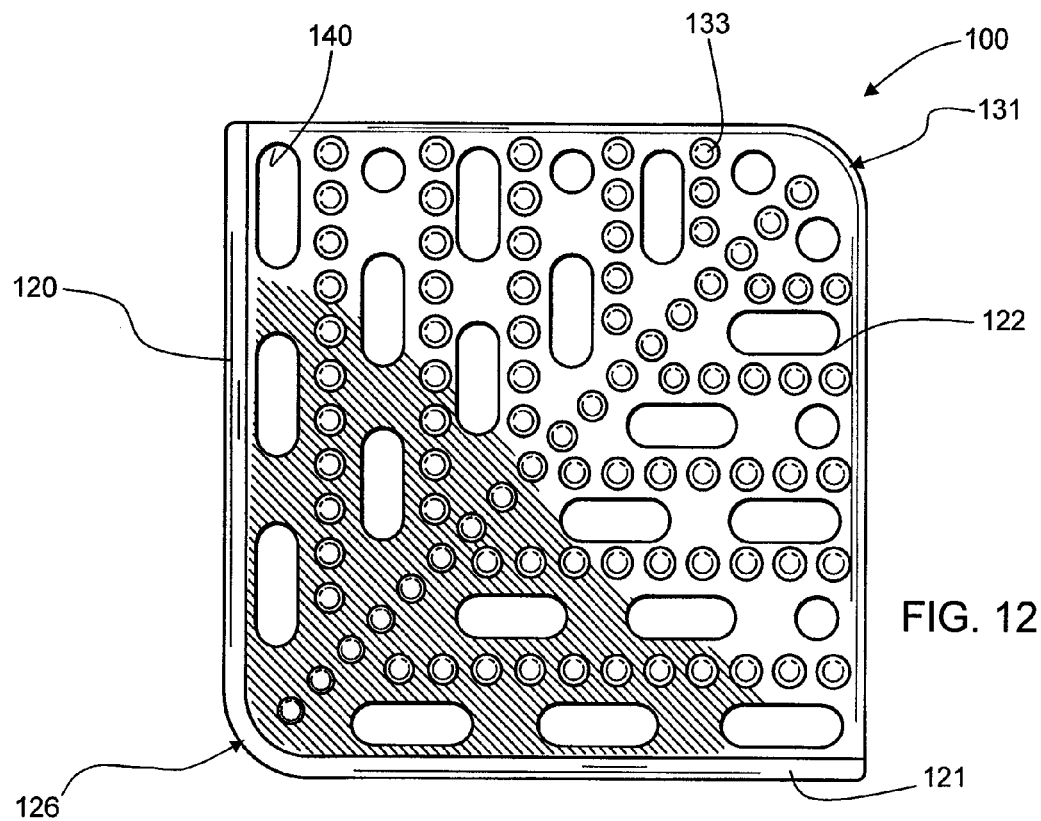
FIG. 12 is a top view of the corner protector of FIG. 11.
Figure 13:
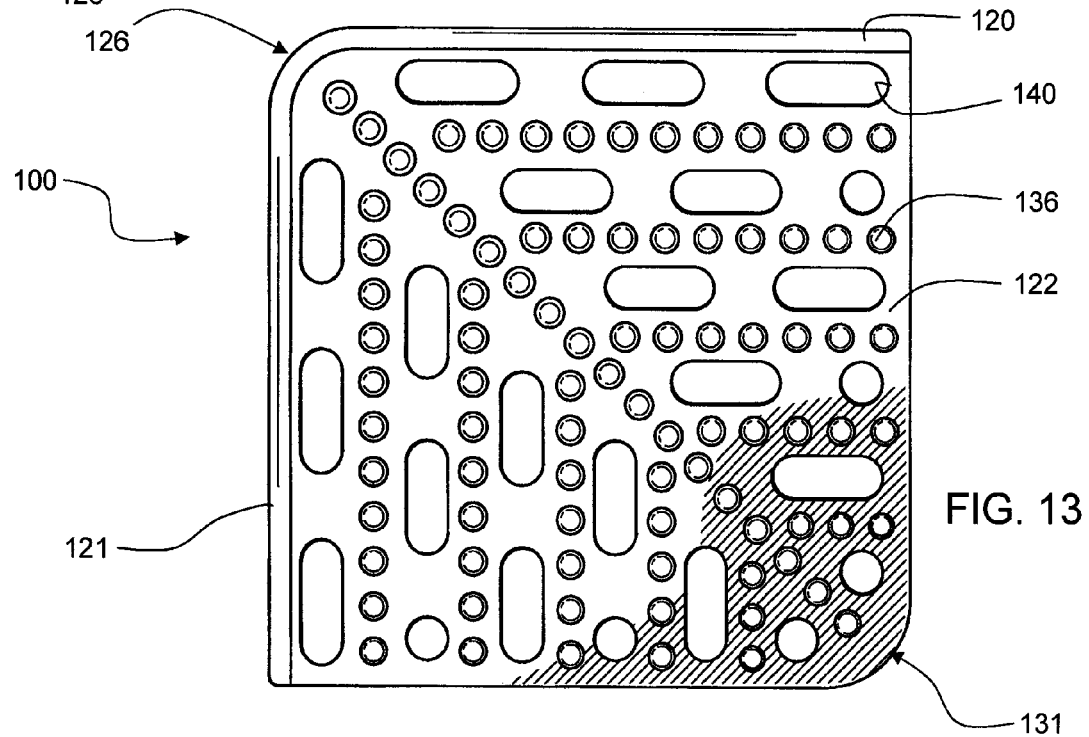
FIG. 13 is a bottom view of the corner protector of FIG. 11.
Figure 14:
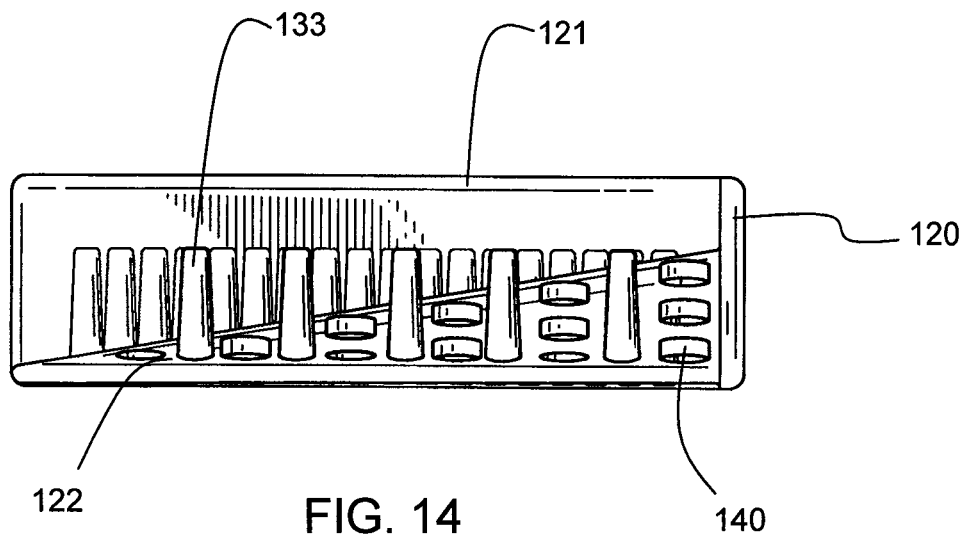
FIG. 14 is a right, front side view of the corner protector of FIG. 11.
Figure 15:
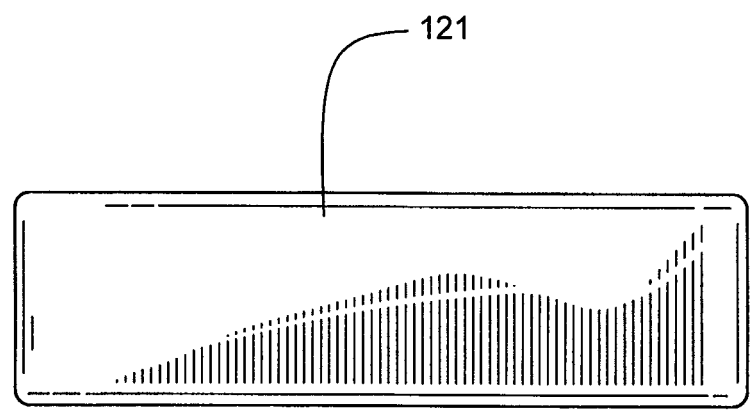
FIG. 15 is a right, rear side view of the corner protector of FIG. 11.
Figure 16:
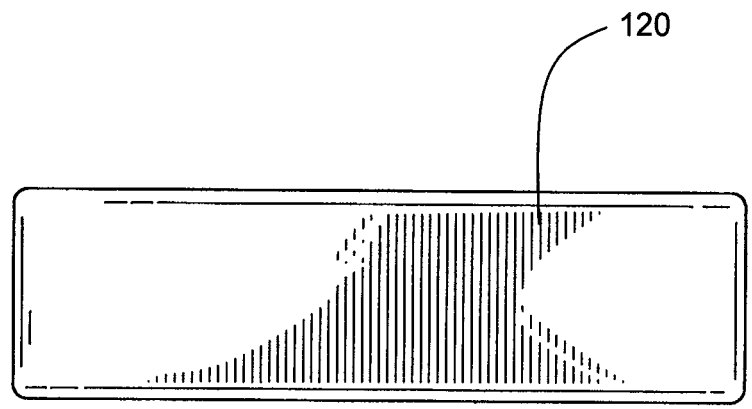
FIG. 16 is a left, rear side view of the corner protector of FIG. 11.
Figure 17:
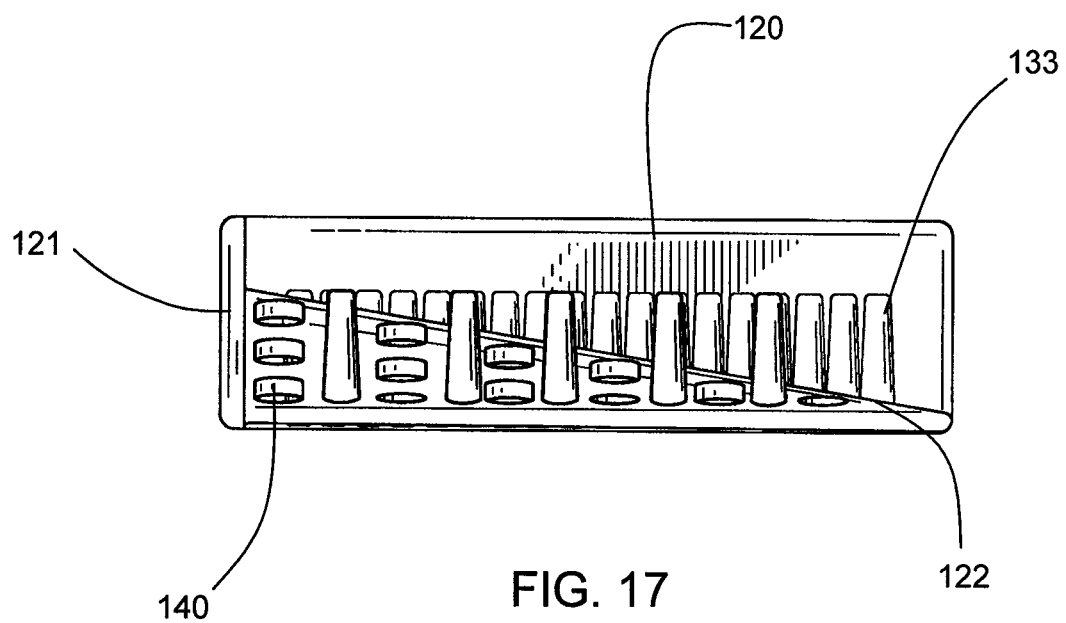
FIG. 17 is a left, front side view of the corner protector of FIG. 11.

Referring to FIGS. 11-17, a surgical tray corner protector according to an embodiment of the invention is shown at reference numeral 100. Like corner protector 10, corner protector 100 includes sides 120 and 121, a sloped base 122, studs 133 and 136, a corner 126 and a front 131, and apertures 140. Unlike corner protector 10, the sides 120 and 121 of the corner protector 100 do not include a sloped portion. As shown in FIGS. 11, 15, and 16, the sides have a constant height "H" to allow for additional protection of the surgical tray 11 when needed.

Referring to FIGS. 18-24, a surgical tray corner protector according to an embodiment of the invention is shown at reference numeral 200. Like corner protector 10, corner protector 200 includes sides 220 and 221, a base 222, a corner 226 and a front 231, and apertures 240. Unlike the base 22, base 222 is a smooth, non-sloping base with a rounded front 231. As shown, the base 222 has a planar top 234 and a planar bottom 237, which allows a tray 11 to rest evenly on the base 222 and the base 222 to rest evenly on the wrap 13. The smoothness of the top and bottom 234 and 237 prevents the protector 200 from sticking to the sterile wrap 13 during and after sterilization. The sides 220 and 221 of the protector 200 are also smooth and have rounded ends 243 to prevent sticking to the wrap 13.

Because the base 222 has a rounded front 231, the sides 220 and 221 extend past the base 222 to create free ends 246 and 247 which are capable of flexing inwardly towards a center of the protector 200 or outwardly away from the center of the protector 200. This arrangement allows the protector 200 to be used with both rounded edge surgical trays and straight edge surgical trays. When used with a rounded tray, the free ends 246 and 247 flex outwardly to allow the rounded tray to be positioned farther back into the protector 200, and thus, the tray may be securely positioned on the base 222 at about its center instead of its edge. When used with a square corner tray, the free ends remain in their natural, non-use position and extend along the sides of the tray.

Figure 18:
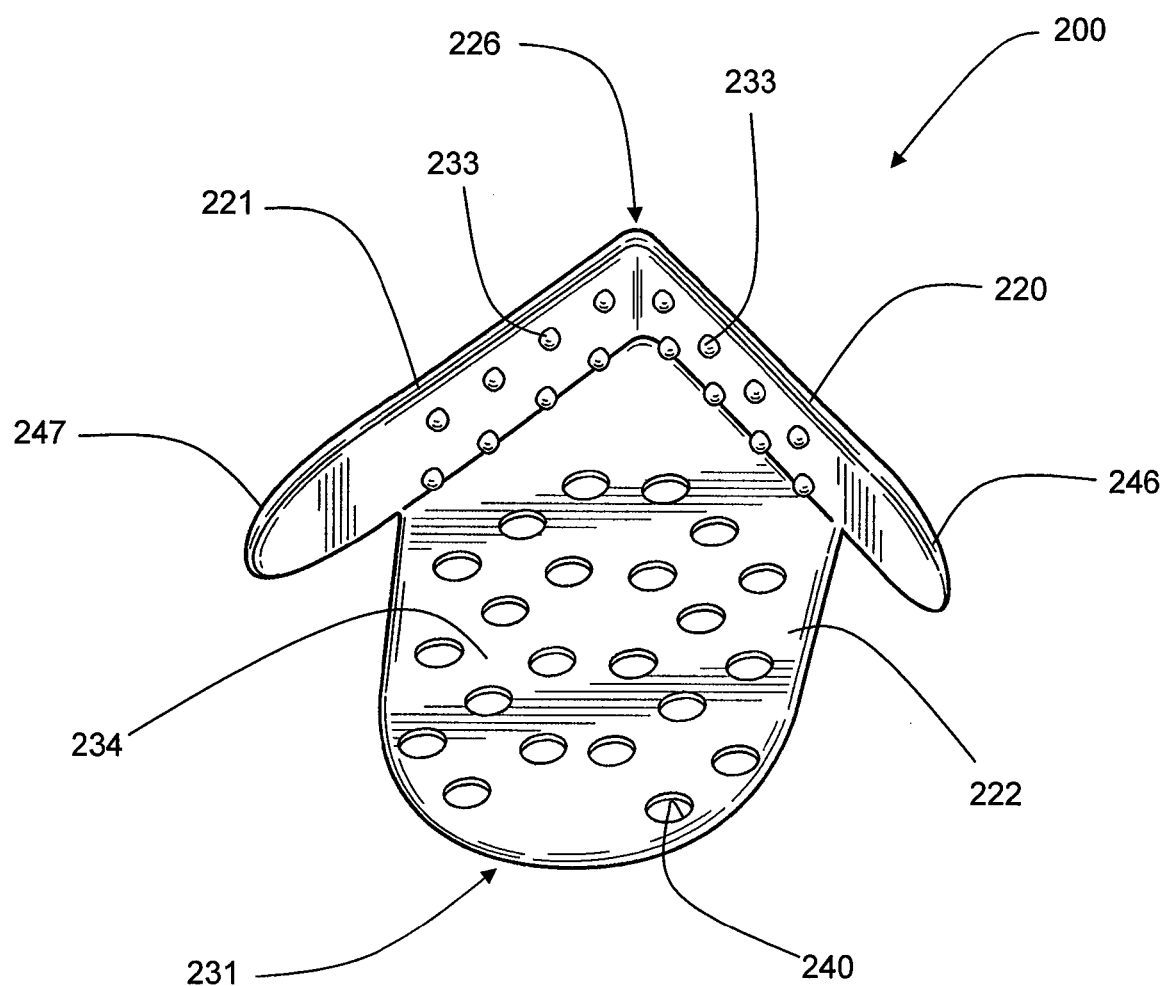
FIG. 18 is a perspective view of a corner protector according to an embodiment of the invention.
Figure 19:
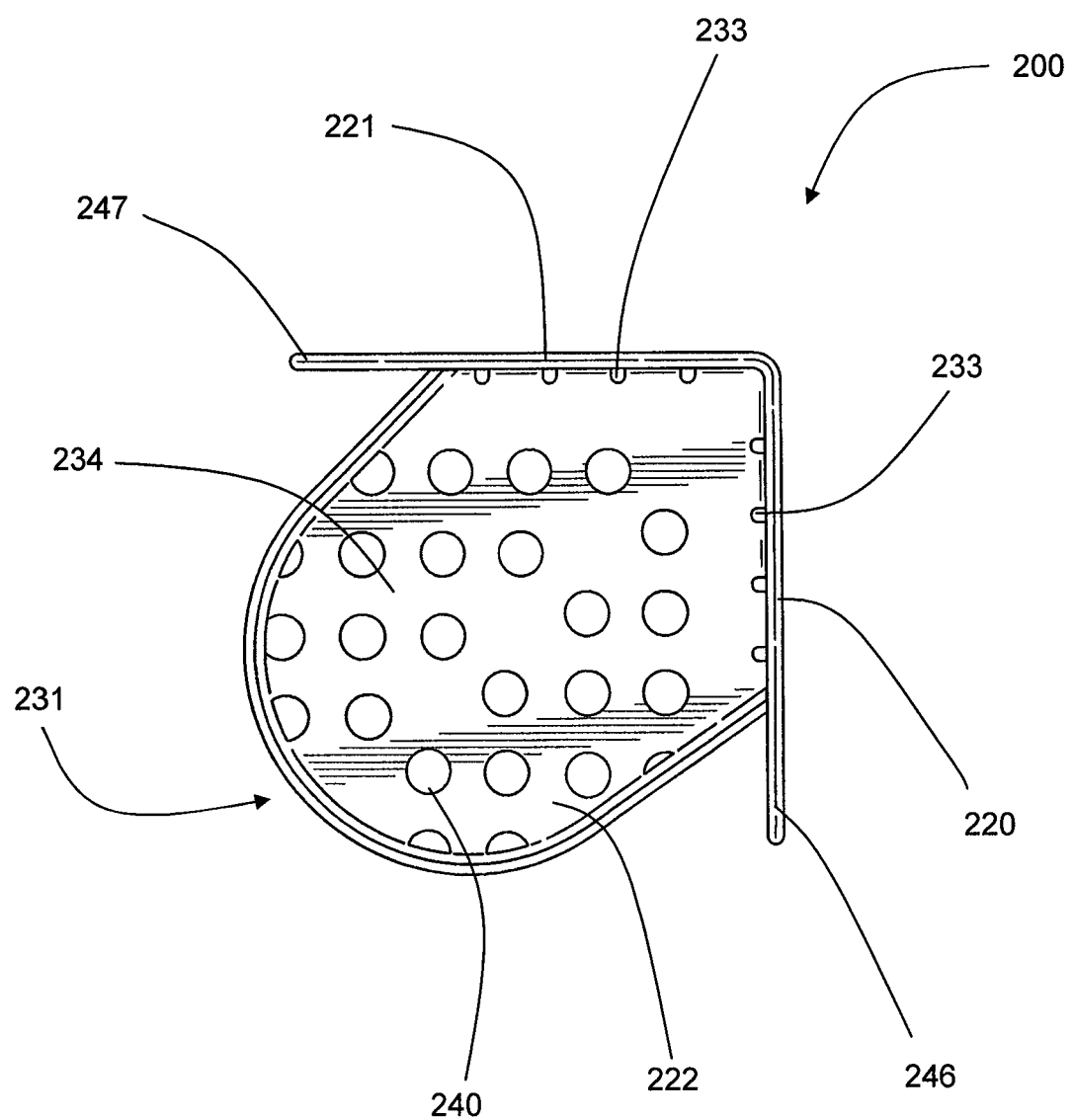
FIG. 19 is a top view of the corner protector of FIG. 18.
Figure 20:
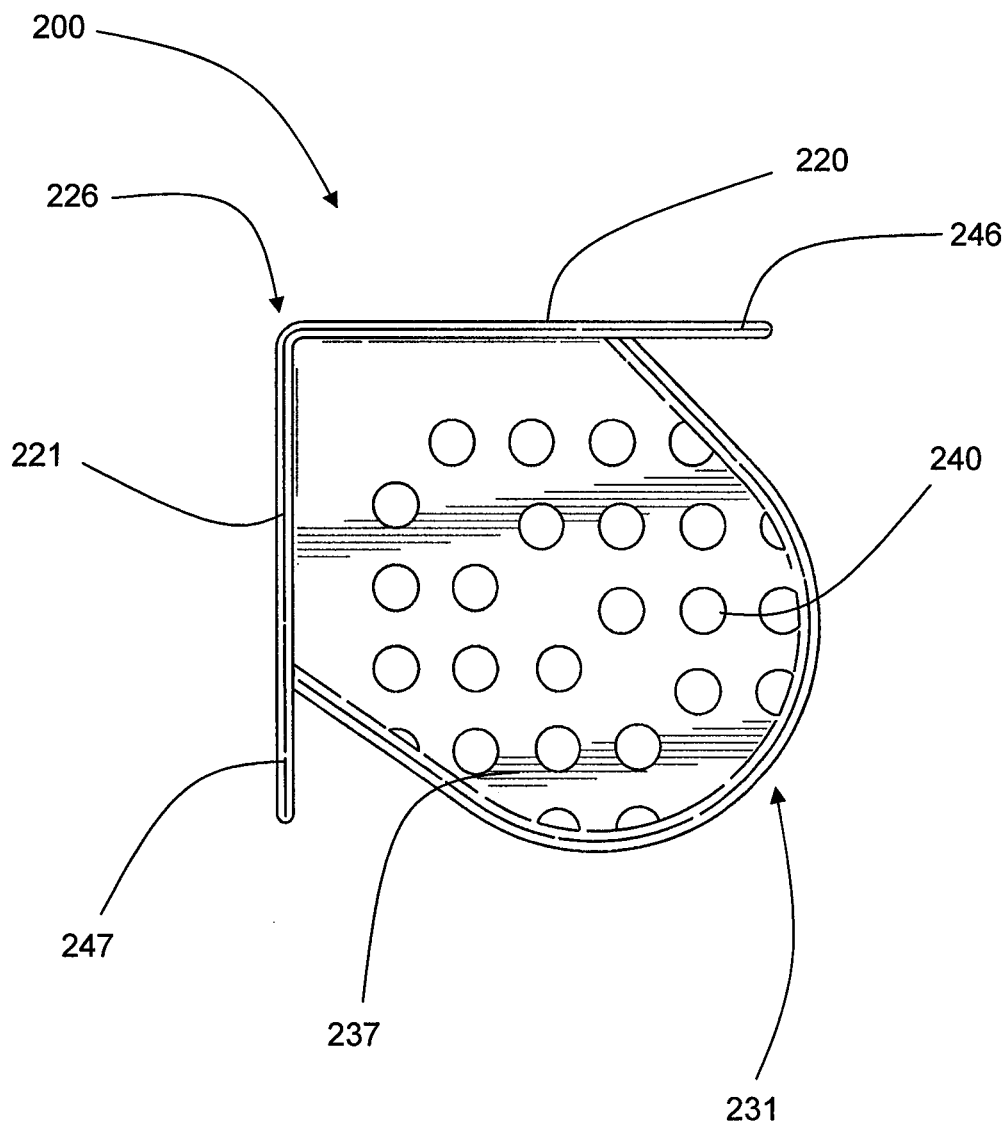
FIG. 20 is a bottom view of the corner protector of FIG. 18.
Figure 21:
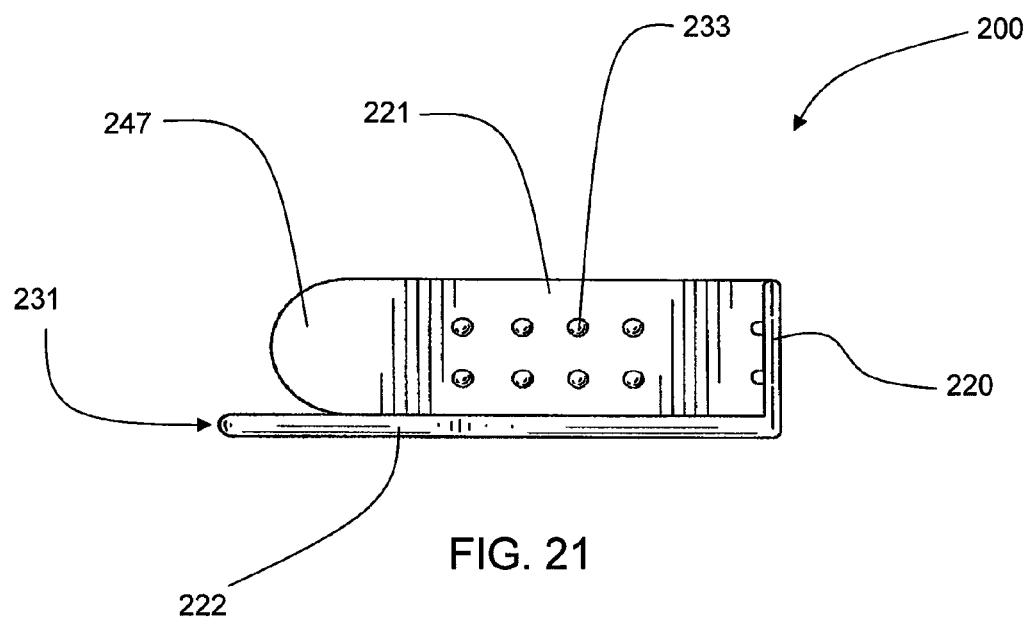
FIG. 21 is a right side view of the corner protector of FIG. 18.
Figure 22:
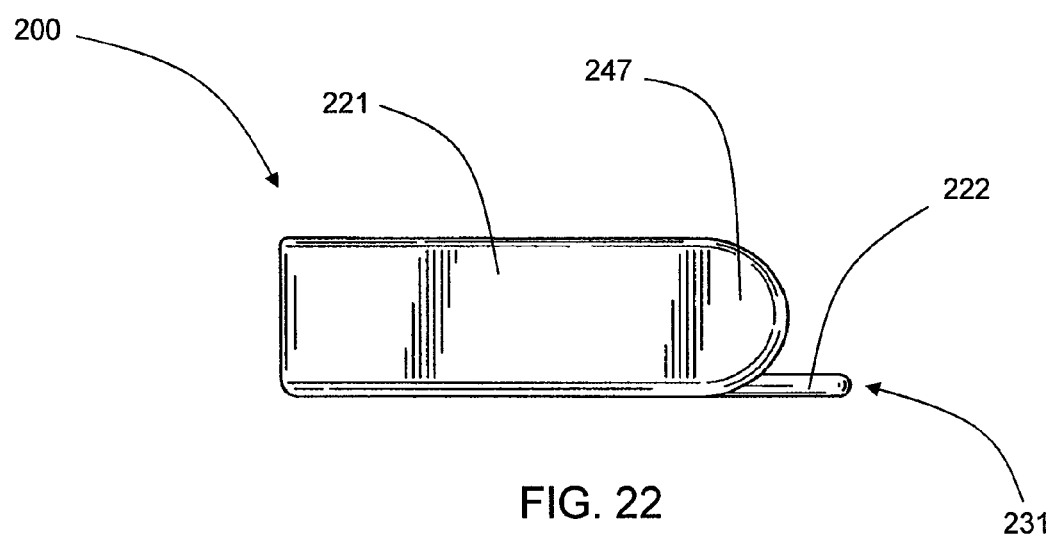
FIG. 22 is a right, rear side view of the corner protector of FIG. 18.
Figure 23:
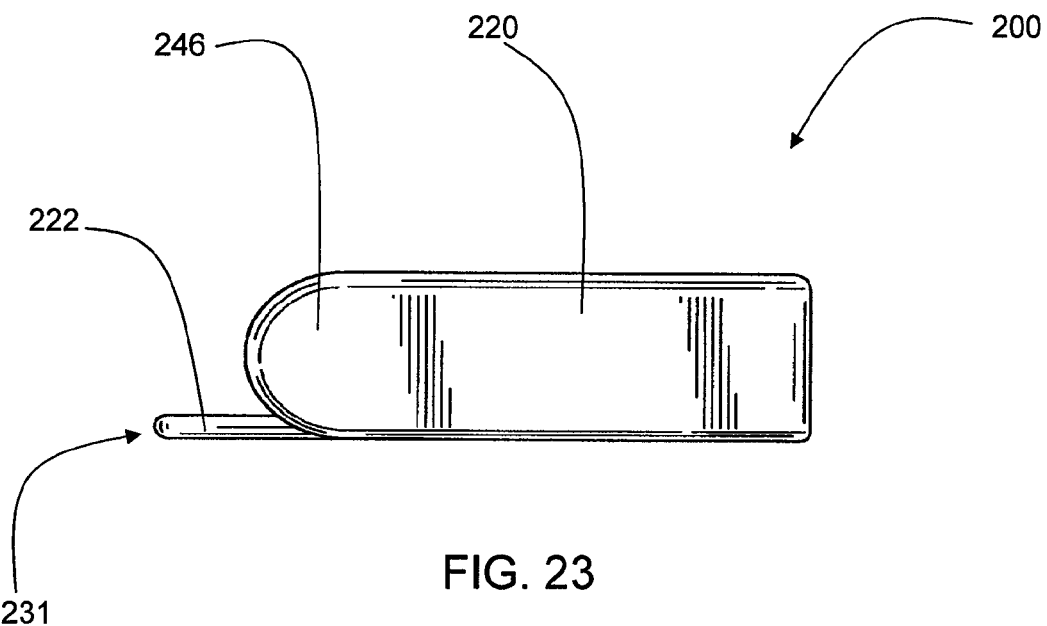
FIG. 23 is a left, rear side view of the corner protector of FIG. 18.
Figure 24:
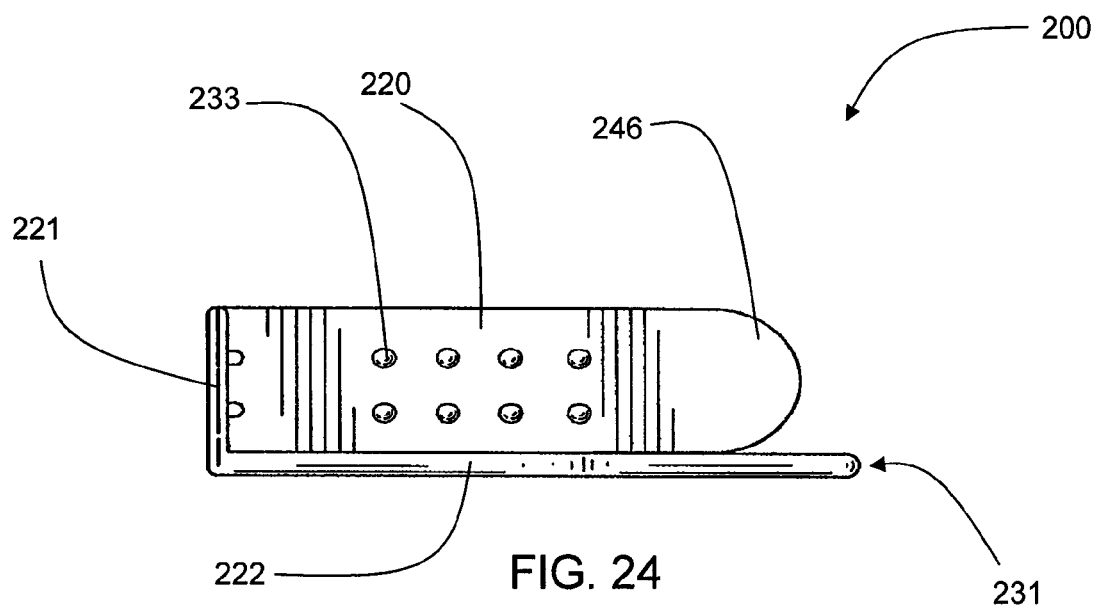
FIG. 24 is a left side view of the corner protector of FIG. 18.

As shown in FIGS. 18 and 19, studs 233 are positioned on an inner surface 249 of the sides 220 and 221. The studs 233 allow the protector 200 to be positioned against the tray 11 without being flush against the tray 11. Thus, the studs 233 create channels 250 between the tray 11 and the sides 220 and 221 of the protector 200. These channels 250 allow the sterilizing agent to flow into the corners of the tray 11 and along its sides between the protector and the tray 11, thereby sterilizing the entire tray 11. Studs 233 may also be placed on the base 222 as shown with respect to corner protector 10.

A surgical tray corner protector is described above. Various details of the invention may be changed without departing from its scope. Furthermore, the foregoing description of the preferred embodiments of the invention and best mode for practicing the invention are provided for the purpose of illustration only and not for the purpose of limitation.

I claim:
1. A corner protector, comprising
(a) a base having a front end and an opposed back end, the back end having first and second edges defining a V-shape; and

(b) first and second sides, each of the sides having spaced-apart, parallel top and bottom edges extending between a proximal end and a distal end, the sides being connected at the proximal ends to form a corner;

(c) wherein a first portion of the bottom edge of the first side adjacent the proximal end of the first side is joined to the first edge of the base and a second portion of the bottom edge of the first side extends beyond the base such that the distal end of the first side is free to flex independently from the base;

(d) wherein a first portion of the bottom edge of the second side adjacent the proximal end of the second side is joined to the second edge of the base and a second portion of the bottom edge of the second side extends beyond the base such that the distal end of the second side is free to flex independently from the base;

(e) wherein the top edges define an open area therebetween free of reinforcement structures to permit a portion of the top edges to move relative to the base.

2. The corner protector according to claim 1, wherein the first and second sides extend upwardly from a top of the base.

3. The corner protector according to claim 1, wherein the protector is made of a medical grade non-moisture retaining material to prevent the development of water borne pathogens.

4. The corner protector according to claim 1, wherein an object is placed on the corner protector such that the base is positioned beneath the object and the first and second sides are positioned along a side of the object.

5. A corner protector adapted to receive a corner of a surgical tray therein, such that the corner protector provides a barrier between a sterile wrap and the corner to prevent tearing of the wrap, the corner protector comprising:

(a) a base;

(b) first and second sides extending upwardly from a top of the base, each of the sides having a bottom edge, wherein a first portion of each bottom edge is connected to the base and a second portion of each bottom edge extends beyond the base such that a distal end of each side is disposed beyond the base;

(c) wherein proximal ends of the first and second sides are joined to each other so as to define a corner, the first and second sides cooperate with the base to define three mutually perpendicular planes that define an open area configured to receive a corner of a surgical tray having a side wall with a height substantially greater than the first and second sides of the corner protector therein.

6. The corner protector according to claim 5, wherein the first and second sides are disposed perpendicular to each other such that they form a continuous L-shaped side.

7. The corner protector according to claim 5, wherein when in an installed position, the surgical tray rests on the base and the first and second sides rest against a side of the surgical tray.

8. The corner protector according to claim 1, wherein at least one aperture extends through the base to allow a medium to pass therethrough.

9. The surgical tray corner protector according to claim 5, wherein a plurality of apertures extend through the base to allow a medium to pass therethrough.

10. A corner protector, comprising:

(a) a base;

(b) first and second sides extending upwardly from a top of the base, each of the sides having spaced-apart top and bottom edges running parallel along a length of each of the sides, wherein a first portion of each bottom edge is connected to the base and a second portion of each bottom edge extends beyond the base such that a distal end of each side is disposed beyond the base and is free to flex independently from the base;

(c) wherein the top edges define an open area free of protrusions therebetween for receiving an object such that the object rests upon the base and the first and second sides reside along a side of the object.

11. A corner protector consisting essentially of:

(a) a base;

(b) planar first and second sides extending upwardly from a top of the base, the sides joined to each other to define a corner, each of the sides having a bottom edge, wherein a first portion of each bottom edge is connected to the base and a second portion of each bottom edge extends beyond the base such that a distal end of each side is free to flex independently from the base, wherein the base and the sides are both formed from medical grade silicone rubber.

\* \* \* \* \*